United States Patent [19]

Hori et al.

[11] Patent Number: 4,684,631
[45] Date of Patent: Aug. 4, 1987

[54] NOVEL 5-FLUORO-2-DEOXYURIDINE DERIVATIVES AND SALTS THEREOF, PROCESS FOR PRODUCING THE SAME, AND ANTITUMOR AGENTS CONTAINING THE SAME

[75] Inventors: Takako Hori; Isao Myokan; Shinji Miyabara, all of Toyama, Japan

[73] Assignee: Toyama Chemical Co., Ltd., Tokyo, Japan

[21] Appl. No.: 781,988

[22] Filed: Sep. 30, 1985

[30] Foreign Application Priority Data

Oct. 9, 1984 [JP] Japan ................................ 59-210525
Jan. 23, 1985 [JP] Japan .................................. 60-9192

[51] Int. Cl.$^4$ ..................... C07H 15/12; A61K 31/70
[52] U.S. Cl. ......................................... 514/51; 536/29
[58] Field of Search ............................ 536/29; 514/51

[56] References Cited

FOREIGN PATENT DOCUMENTS 767195  5/1971  Belgium .
0767195 5/1971  France ................................... 53/29
0457056 11/1970 Japan ................................... 536/29
0093096 5/1984  Japan ................................... 536/29
59-93096 5/1984  Japan .

OTHER PUBLICATIONS

Hunston et al, J. Med. Chem., 27, 440–444, (1984).
Whitemore, Organic Chemistry, Second Edition, vol. 1, Dover Publications, pp. 178–179.
Nomenclature of Organic Chemistry, 1979 Edition, Pergamon Press, pp. 141–143.
Burger's Medicinal Chemistry, Fourth Edition, Part II, John Wiley & Sons, pp. 608–611.

Primary Examiner—Johnnie R. Brown
Assistant Examiner—F. T. Moezie
Attorney, Agent, or Firm—Oblon, Fisher, Spivak, McClelland & Maier

[57] ABSTRACT

This invention relates to a novel 5-fluoro-2'-deoxyuridine derivative and a salt thereof which have an antitumor effect on mammals, a process for producing the same, and an antitumor agent containing the same.

16 Claims, No Drawings

NOVEL 5-FLUORO-2-DEOXYURIDINE DERIVATIVES AND SALTS THEREOF, PROCESS FOR PRODUCING THE SAME, AND ANTITUMOR AGENTS CONTAINING THE SAME

This invention relates to a novel 5-fluoro-2'-deoxyuridine derivative and a salt thereof which have an antitumor effect on mammals, a process for producing the same, and an antitumor agent containing the same.

It has heretofore been known that 5-fluoro-2'-deoxy-$\beta$-uridine (commonly called FudR) has a stronger cytocidal activity than 5-fluorouracil (commonly called 5-Fu) in vitro [C. Heidelberger et al., Cancer Res., 28, 2529–2538 (1968)].

Also, it has been considered that FudR is converted to 5-fluoro-2'-deoxyuridine-5'-monophosphate (commonly called FduMP) in cells, and this inhibits thymidylate synthetase and consequently inhibits DNA synthesis, whereby a carcinostatic activity is exhibited [C. Heidelberger et al., Mol. Pharmacol., 1, 14–30 (1965)].

However, clinically FudR is only equivalent in efficacy to 5-Fu, and also has a high toxicity, so that it is now used as an intra-arterial infusion in the U.S.A. [Physicians' Desk Reference, 32 edition, 1387 (1978)].

Furthermore, FudR is rapidly excreted in vivo, poor in persistency, easily cleaved by nucleoside phosphorylase, and metabolized to $\alpha$-fluoro-$\beta$-alanine through 5-Fu [C. Heidelberger, Cancer Res., 30, 1549–1569 (1970)], and therefore, the properties thereof as a time-dependent antimetabolite having a thymidylate synthetase-inhibitory activity are not sufficiently exhibited.

Moreover, FduMP is the active form of FudR; however, FduMP per se is not taken up by cells. After FduMP has been converted to FudR in the exterior of cell, it enters the cell and is converted into the active form FduMP again to exhibit an antitumor activity [R. N. Hunston et al., J. Med. Chem., 27, 440–444 (1984)]. Therefore, FduMP has the same disadvantages as does FudR.

Under such circumstances, the present inventors have made extensive research for the purpose of finding a FudR derivative which is prevented from being degraded in vivo, has a strong antitumor activity and has a low toxicity. As a result, they have found that a 5-fluoro-2'-deoxyuridine derivative having a group represented by the formula,

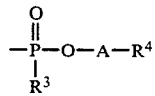

in which $R^3$ represents an oxido group or a hydroxyl group; A represents a lower alkylene group; and $R^4$ represents a substituted or unsubstituted trialkylammonio, cyclic ammonio or cyclic amino group, introduced into one of the hydroxyl groups at the 3'- and 5'-positions of the FudR, said derivative being a kind of phospholipid, and a salt of said derivative have an antitumor effect on mammals.

An object of this invention is to provide a novel 5-fluoro-2'-deoxyuridine derivative and a salt thereof.

Another object of this invention is to provide a process for producing the above novel 5-fluoro-2'-deoxyuridine derivative or a salt thereof.

A further object of this invention is to provide an antitumor agent containing the novel 5-fluoro-2'-deoxyuridine derivative or a salt thereof.

According to this invention, there is provided a 5-fluoro-2'-deoxyuridine derivative represented by the general formula [I] or a salt thereof:

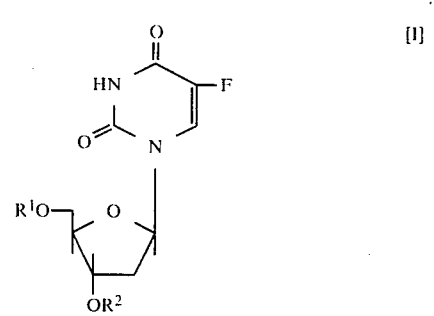

wherein $R^1$ and $R^2$ are different from each other, one of which represents a $C_{1-30}$aliphatic carboxylic acid residue and the other represents a group represented by the formula,

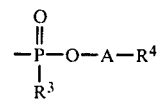

in which $R^3$ represents an oxido group or a hydroxyl group, A represents a lower alkylene group and $R^4$ represents a substituted or unsubstituted trialkylammonio, cyclic quaternary ammonio or cyclic amino group.

This invention further provides a process for producing a 5-fluoro-2'-deoxyuridine derivative represented by the general formula [I] or a salt thereof, and also provides an antitumor agent containing a 5-fluoro-2'-deoxyuridine derivative represented by the general formula [I] or a salt thereof.

In $R^1$ and $R^2$, the $C_{1-30}$aliphatic carboxylic acid residue includes $C_{1-30}$-saturated and $C_{3-30}$-unsaturated aliphatic carboxylic acid residues. The $C_{1-30}$-saturated aliphatic carboxylic acid residues include, for example, formyl and $C_{2-30}$alkanoyl groups such as acetyl, propionyl, butyryl, valeryl, hexanoyl, octanoyl, decanoyl, lauroyl, myristoyl, palmitoyl, stearoyl, eicosanoyl, docosanoyl and the like, and the $C_{3-30}$-unsaturated aliphatic carboxylic acid residues include, for example, $C_{3-30}$alkenoyl groups such as 9-hexadecenoyl, oleoyl, cis-9, cis-12-octadecadienoyl, 9,12,15-octadecatrienoyl and the like.

In A, the lower alkylene group includes, for example, straight and branched chain $C_{1-5}$alkylene groups such as methylene, ethylene, trimethylene, propylene, tetramethylene, pentamethylene and the like.

In $R^4$, the trialkylammonio group includes, for example, tri-$C_{1-4}$alkylammonio groups such as trimethylammonio, triethylammonio, dimethylethylammonio, diethylmethylammonio, tripropylammonio, tributylammonio and the like.

In $R^4$, the cyclic quaternary ammonio group includes, for example, pyridinio, pyridazinio, pyrimidinio, pyrazinio, 2H-imidazolio, 3H-imidazolio, 2H-pyrazolio, 1-methylpiperidinio, 4-methylmorpholinio, 2H-1,2,4-triazol-1-io and the like. Also, the cyclic amino group includes, for example, 1-pyrrolyl, 1-pyrrolinyl, imidazolyl, 1-pyrazolyl, 2-imidazolin-1-yl and the like.

Furthermore, the trialkylammonio, cyclic quaternary ammonio and cyclic amino groups explained above may be substituted by a hydroxyl group, a $C_{1-4}$alkoxy group such as methoxy, ethoxy or the like; an acyloxy group such as acetyloxy, propionyloxy or the like; a $C_{1-4}$alkyl group such as methyl, ethyl, propyl, butyl or the like; or a di-$C_{1-4}$alkylamino group such as dimethylamino or the like.

Also, the salt of the compound represented by the general formula [I] may be any pharmaceutically acceptable salt, and includes, for example, salts with inorganic acids such as hydrochloric acid, hydrobromic acid, sulfuric acid, phosphoric acid and the like; salts with organic acids such as acetic acid, lactic acid, tartaric acid, methanesulfonic acid, benzenesulfonic acid, p-toluenesulfonic acid and the like; salts with alkali metals such as sodium, potassium and the like; salts with alkaline earth metals such as magnesium, calcium, barium and the like; etc.

$R^3$ represents an oxido group or a hydroxyl group, and when $R^3$ is an oxido group and $R^4$ is a substituted or unsubstituted trialkylammonio or cyclic quaternary ammonio group, said oxido group usually forms an inner salt with the substituted or unsubstituted trialkylammonio or cyclic ammonio group in $R^4$ mentioned above.

Also, this invention includes optical isomers and geometric isomers of the compound represented by the general formula [I] and its salt, and further includes all hydrates and crystal forms thereof.

Next, the process for producing the compound represented by the general formula [I] or a salt thereof is explained below.

The compound of the general formula [I] and the salt thereof which are of this invention can be produced by, for example, the following process:

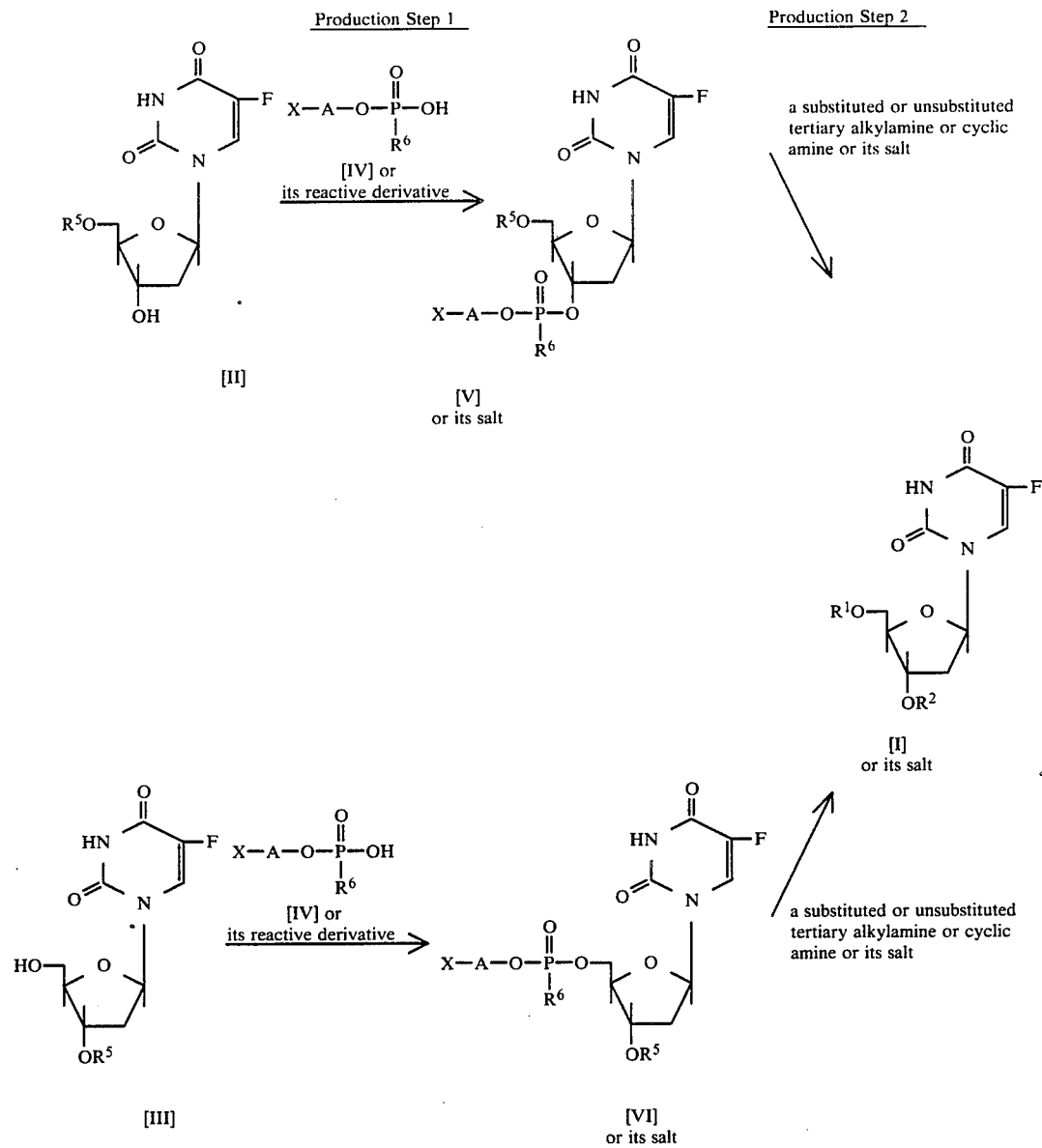

wherein $R^1$, $R^2$ and A have the same meanings as defined above; $R^5$ is a $C_{1-30}$aliphatic carboxylic acid residue; $R^6$ is a halogen atom or a protected or unprotected hydroxyl group; and X is a removable group.

In $R^6$, the halogen atom includes fluorine, chlorine, bromine, iodine and the like, and the protected hydroxyl group includes 2,2,2-trichloroethyloxy, 2-(2-pyridyl)ethyloxy, diphenylmethyloxy, p-nitrobenzyloxy, phenoxy and the like.

In $R^5$, the $C_{1-30}$aliphatic carboxylic acid residue includes the $C_{1-30}$aliphatic carboxylic acid residues mentioned as to $R^1$ and $R^2$.

The substituted or unsubstituted tertiary alkylamine and cyclic amine to be used in Production Step 2 includes tertiary alkylamines and cyclic amines capable of being converted into the substituted or unsubstituted trialkylammonio, cyclic quaternary ammonio and cyclic amino groups mentioned as to $R^4$.

The removable group for X includes, for example, halogen atoms such as fluorine, chlorine, bromine, iodine and the like; arenesulfonyloxy groups such as benzenesulfonyloxy, p-toluenesulfonyloxy and the like; etc.

The salt of the compound represented by the general formula [V] or [VI] includes, for example, salts with alkali metals such as sodium, potassium and the like; salts with alkaline earth metals such as magnesium, calcium, barium and the like; etc. Also, the salt of the substituted or unsubstituted tertiary alkylamine or cyclic amine includes, for example, salts with inorganic acids such as hydrochloric acid, hydrobromic acid, sulfuric acid and the like; salts with organic acids such as methanesulfonic acid, benzenesulfonic acid, p-toluenesulfonic acid and the like; etc.

The reactive derivative of the compound represented by the general formula [IV] includes, for example, those of the phosphoryl halide type, the phosphoryl imidazole type, the phosphoryl triazole type and the like.

The compound represented by the general formula [II] or [III] can be produced in a manner known per se or a similar manner, for example, by the method described in C. Heidelberger et al., Biochemical Pharmacology, 14, 1605–1619 (1965), or the like.

Next, the production process is described in more detail below.

Production Step 1

The reaction of the compound represented by the general formula [IV] or the reactive derivative thereof with the compound represented by the general formula [II] or [III] is carried out in the presence or absence of a solvent inert to the reaction. The solvent used in this reaction includes, for example, ketones such as acetone, methyl ethyl ketone and the like; ethers such as diethyl ether, diisopropyl ether, tetrahydrofuran, dioxane and the like; nitriles such as acetonitrile, propionitrile and the like; aromatic hydrocarbons such as benzene, toluene and the like; halogenated hydrocarbons such as 1,1-dichloroethane, methylene chloride, chloroform and the like; esters such as ethyl acetate, butyl acetate and the like; amides such as N,N-dimethylformamide, N,N-dimethylacetamide and the like; etc., and these solvents may be used alone or in admixture of two or more.

Also, the above reaction may be effected in the presence of a base, and this base includes, for example, inorganic bases such as sodium carbonate, potassium carbonate, silver oxide and the like; and organic bases such as triethylamine, tripropylamine, tributylamine, N-methylmorpholine, N,N-dimethylaniline, N,N-diethylaniline, pyridine, 2,6-lutidine, quinaldine and the like. The amount of the base used is at least equimolar to, preferably 1.0 to 2.0 moles per mole of, the compound of the general formula [II] or [III].

When the compound represented by the general formula [IV] is used in the form of a free acid, an appropriate condensing agent may be used, and this condensing agent includes, for example, N,N'-di-substituted carbodiimides such as N,N'-dicyclohexylcarbodiimide, N-cyclohexyl-N'-morpholinoethylcarbodiimide, N-cyclohexyl-N'-(4-diethylaminocyclohexyl)carbodiimide, N-ethyl-N'-(3-dimethylaminopropyl)carbodiimide and the like; triphenylphosphine-2,2-dipyridyl disulfide; arenesulfonyl chlorides such as benzenesulfonyl chloride, 2,4,6-triisopropylbenzenesulfonyl chloride and the like; etc. The amount of the condensing agent used is at least equimolar to the free acid represented by the general formula [II] or [III].

The above reaction may be carried out usually at a temperature of $-50°$ to $100°$ C., preferably $0°$ to $30°$ C., for a period of 10 minutes to 48 hours.

The amount of the compound represented by the general formula [IV] or the reactive derivative thereof used is at least equimolar to, preferably 1.0 to 2.0 moles per mole of, the compound represented by the general formula [II] or [III].

Production Step 2

The reaction of the compound represented by the general formula [V] or [VI] or the salt thereof with the substituted or unsubstituted tertiary alkylamine or cyclic amine or the salt thereof is usually carried out in a solvent inert to the reaction, and this solvent includes, for example, ketones such as acetone, methyl ethyl ketone and the like; ethers such as diethyl ether, diisopropyl ether, tetrahydrofuran, dioxane and the like; aromatic hydrocarbons such as benzene, toluene and the like; halogenated hydrocarbons such as 1,1-dichloroethane, methylene chloride, chloroform and the like. These solvents may be used alone or in admixture of two or more. When the substituted or unsubstituted tertiary alkylamine or cyclic amine is liquid, the compound may be used in excess to allow the compound per se to act as a solvent.

The reaction temperature and the reaction time are not critical; however, the reaction is usually effected at a temperature of $10°$ to $80°$ C. and is completed in a period of 5 minutes to 140 hours.

The amount of the substituted or unsubstituted tertiary alkylamine or cyclic amine or the salt thereof is used in an amount at least equimolar to the compound represented by the general formula [V] or [VI] or a salt thereof.

The compound represented by the general formula [I] is in some cases obtained in the form of a salt with the removed X; however, the salt may, if necessary, be treated with an ion-exchange resin or a silver ion after the reaction to convert it into a corresponding inner salt. Also, the salt may be converted into another salt in a manner known per se.

After the reaction in Production Step 1 or 2 has been completed, the reaction mixture may be subjected to a column chromatography and/or recrystallization according to a conventional manner to purify and isolate the compound represented by the general formula [I], [V] or [VI]. When a stereoisomer is present in the isolated product, the product may, if necessary, be treated by a conventional optical resolution method to isolate the isomer.

The various reaction conditions in the above production processes are not restricted to those mentioned above, and may be appropriately varied depending upon the kind of the reactants.

The compound represented by the general formula [V] or [VI] and the salt thereof which are the starting materials in Production Step 2 are novel, and are useful intermediates for producing, for example, the compound represented by the general formula [I] or the salt thereof.

Furthermore, the compound represented by the general formula [V] or [VI] obtained in Production Step 1 may be used after isolation or without isolation in Production Step 2.

When $R^6$ of the compound represented by the general formula [V] or [VI] is a halogen atom or a protected hydroxyl group, it may be hydrolyzed or the hydroxyl-protecting group may be removed to obtain the compound represented by the general formula [V] or [VI] in which $R^6$ is a hydroxyl group.

Pharmacological activities of typical compounds of this invention are described below.

Test compounds

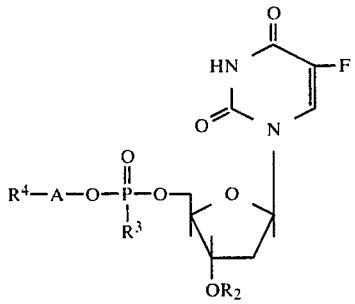

| Test compd. No. | $R^2$ | $R^3$ | $R^4$—A— |
|---|---|---|---|
| 1 | —C(=O)(CH$_2$)$_{14}$CH$_3$ | O$^\ominus$ | (CH$_3$)$_3$N$^\oplus$—CH$_2$CH$_2$— |
| 2 | —C(=O)(CH$_2$)$_{16}$CH$_3$ | O$^\ominus$ | (CH$_3$)$_3$N$^\oplus$CH$_2$CH$_2$— |
| 3 | —C(=O)(CH$_2$)$_7$CH=CH(CH$_2$)$_7$CH$_3$ | O$^\ominus$ | (CH$_3$)$_3$N$^\oplus$CH$_2$CH$_2$— |
| 4 | —C(=O)(CH$_2$)$_{14}$CH$_3$ | O$^\ominus$ | (CH$_3$)$_2$N—C$_6$H$_4$—N$^\oplus$—CH$_2$CH$_2$— |
| 5 | CH$_3$(CH$_2$)$_{14}$CO— | O$^\ominus$ | (CH$_3$)$_3$N$^\oplus$—CH$_2$CH$_2$— |
| 6 | CH$_3$(CH$_2$)$_{16}$CO— | O$^\ominus$ | (CH$_3$)$_3$N$^\oplus$—CH$_2$CH$_2$— |
| 7 | CH$_3$(CH$_2$)$_{10}$CO— | O$^\ominus$ | (CH$_3$)$_3$N$^\oplus$—CH$_2$CH$_2$— |
| 8 | CH$_3$(CH$_2$)$_7$CH=CH(CH$_2$)$_7$CO— | O$^\ominus$ | (CH$_3$)$_3$N$^\oplus$—CH$_2$CH$_2$— |
| 9 | CH$_3$(CH$_2$)$_4$CO— | O$^\ominus$ | (CH$_3$)$_3$N$^\oplus$—CH$_2$CH$_2$— |
| 10 | CH$_3$(CH$_2$)$_{14}$CO— | O$^\ominus$ | HN—(imidazole)—N$^\oplus$—CH$_2$CH$_2$— |
| 11 | CH$_3$(CH$_2$)$_{14}$CO— | O$^\ominus$ | HOCH$_2$CH$_2$—N$^\oplus$(CH$_3$)$_2$—CH$_2$CH$_2$— |
| 12 | CH$_3$(CH$_2$)$_{14}$CO— | O$^\ominus$ | O(morpholino)N$^\oplus$(CH$_3$)—CH$_2$CH$_2$— |

(1) Antitumor effect

Eight ddY strain mice (male, 5 weeks old, weight: about 25 g) per group were used, and $5\times10^6$ Ehrlich carcinoma cells were inoculated subcutaneously into the inguinal region of the mice. The test compound dissolved or suspended in a physiological saline solution was intraperitoneally administered to the mice once daily for 6 days from the day after the inoculation. As the control compound, FudR was used. To the control group was administered only the physiological saline solution. On the 12th day after the inoculation, the weight of the tumor was measured, and the antitumor activity was indicated by the ratio of said weight to that of the control group to which only the physiological saline solution was administered (T/C (%)).

The results obtained are shown in Table 1.

TABLE 1

| Test compound No. | Dosage (μmole/kg/day) | Effect (T/C (%)) |
|---|---|---|
| 1 | 3 | 47 |
|  | 10 | 19 |
|  | 30 | 15 |
| 2 | 3 | 22 |
|  | 10 | 19 |
| 3 | 3 | 38 |
|  | 10 | 21 |
| 4 | 3 | 66 |
|  | 10 | 34 |
| FudR | 3 | 87 |
|  | 10 | 67 |
|  | 30 | 42 |
| 5 | 1 | 38 |
|  | 3 | 17 |
| 6 | 1 | 24 |
|  | 3 | 10 |
| 7 | 1 | 40 |
|  | 3 | 27 |
| 8 | 1 | 50 |
|  | 3 | 28 |
| 9 | 1 | 50 |
|  | 3 | 32 |
| 10 | 1 | 42 |
|  | 3 | 36 |
|  | 10 | 18 |
| 11 | 1 | 41 |
|  | 3 | 44 |
|  | 10 | 22 |
| 12 | 1 | 46 |
|  | 3 | 28 |
| FudR | 3 | 87 |
|  | 10 | 77 |

(2) Acute toxicity test

To ddY mice (male, 5 weeks old, 5 mice per group) was intraperitoneally administered the test compound dissolved or suspended in a physiological saline solution only one time. On the 14th day after the administration, the death of mouse was judged, and the $LD_{50}$ value was calculated.

The results obtained are shown in Table 2.

TABLE 2

| Test compound No. | $LD_{50}$ value (mg/kg) |
|---|---|
| 1 | 208 |
| 2 | 188 |
| 3 | 200 |
| 5 | >200 |
| 6 | 200 |
| 7 | >300 |
| 8 | 300 |

TABLE 2-continued

| Test compound No. | $LD_{50}$ value (mg/kg) |
|---|---|
| 9 | 500 |

As is clear from the above results, the compound of the general formula [I] and the salt thereof which are of this invention have an excellent antitumor activity and a low toxicity, and therefore, are compounds useful as an antitumor agent.

When the compound of the general formula [I] and the salt thereof are used as medicines, they may be orally or parenterally administered as such or in admixture with an appropriate amount of additives such as excipients, carriers, diluents and the like in the form of a tablet, capsule, granule, powder, injection, suppository or the like. The dosage of the compound is usually 1 to 500 mg or so per adult a day, and this amount of compound is administered in one or several portions; however, the dosage may be appropriately varied depending upon the age, weight and symptom of a patient.

This invention is further explained below referring to Examples and Preparation Examples. However, this invention is not limited to the Examples and Preparation Examples.

EXAMPLE 1

(1)
5-Fluoro-2'-deoxy-3'-O-palmitoyl-β-uridine-5'-(2-bromoethly)phosphate

In 10 ml of anhydrous tetrahydrofuran were dissolved 0.26 g of 2,6-lutidine and 0.58 g of 2-bromoethyl phosphorodichloridate, and a solution of 0.97 g of 5-fluoro-2'-deoxy-3'-O-palmitoyl-β-uridine in 10 ml of anhydrous tetrahydrofuran was dropped into the resulting solution over 10 minutes with stirring under ice-cooling. After completion of the dropping, the resulting mixture was subjected to reaction at room temperature with stirring overnight. Subsequently, the reaction mixture was concentrated under reduced pressure. To the residue thus obtained were added 10 ml of water, 20 ml of chloroform and 2 ml of triethylamine, and the resulting mixture was stirred for one hour under ice-cooling and further stirred at room temperature for one hour. Subsequently, the pH of the mixture was adjusted to 1.0 with dilute hydrochloric acid, and 20 ml of methanol was added thereto, after which the organic layer was separated. The solvent was removed by distillation under reduced pressure, and the residue thus obtained was purified by a column chromatography (Wako Silica Gel C-200, eluant: chloroform:methanol=50:1-10:1 by volume) to obtain 1.05 g of white, amorphous 5-fluoro-2'-deoxy-3'-O-palmitoyl-β-uridine-5'-(2-bromoethyl)-phosphate (yield 78%).

IR (KBr) cm$^{-1}$: 2920, 2850, 1720, 1700, 1680, 1460, 1355, 1250, 1180, 1100, 1060, 1020

NMR (CDCl$_3$:CD$_3$OD=2:1 mixture) δ values: 0.89 (t, 3H, J=5 Hz), 1.03–1.80 (m, 26H), 2.00–2.60 (m, 4H), 3.55 (t, 2H, J=6 Hz), 3.91–4.56 (m, 5H), 5.16–5.50 (m, 1H), 6.08–6.48 (m, 1H), 7.81 (d, 1H, J=6 Hz)

Reaction was effected in the same manner as above to obtain the compounds shown in Table 3.

Further, the same procedure as above was repeated, except that 5-fluoro-2'-deoxy-5'-O-acryl-β-uridine was substituted for the 5-fluoro-2'-deoxy-3'-O-palmitoyl-β-uridine to obtain the compounds shown in Table 4.

TABLE 3

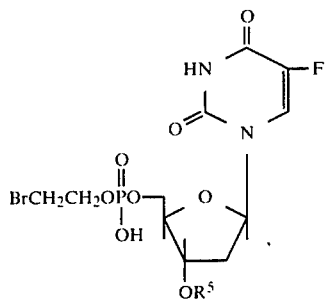

| Compound R[5] | State | IR cm[-1] | NMR (CDCl$_3$:CD$_3$OD = 1) δ value | Yield (%) |
|---|---|---|---|---|
| CH$_3$(CH$_2$)$_{16}$C(O)— | White, amorphous | (KBr) 2920, 2850, 1720, 1700, 1680, 1460, 1355, 1250, 1180, 1100, 1050, 1020 | 0.89 (t, 3H, J=5Hz), 1.05–1.85 (m, 30H), 2.05–2.60 (m, 4H), 3.55 (t, 2H, J=6Hz), 3.91–4.57 (m, 5H), 5.20–5.50 (m, 1H), 6.10–6.50 (m, 1H), 7.86 (d, 1H, J=6Hz) | 75 |
| CH$_3$(CH$_2$)$_7$CH=CH(CH$_2$)$_7$C(O)— | Waxy | (KBr) 2920, 2850, 1720, 1670, 1460, 1250, 1180, 1100, 1060, 1020 | 0.89 (t, 3H, J=5Hz), 1.05–1.80 (m, 22H), 1.80–2.60 (m, 8H), 3.55 (t, 2H, J=6Hz), 3.95–4.53 (m, 5H), 5.08–5.50 (m, 3H), 6.10–6.44 (m, 1H), 7.83 (d, 1H, J=6Hz) | 74 |
| CH$_3$(CH$_2$)$_4$C(O)— | Oily | (Neat) 2950, 2860, 1720, 1660, 1460, 1260, 1200, 1100, 1050, 1010 | 0.89 (t, 3H, J=5Hz), 1.07–1.90 (m, 6H), 2.02–2.60 (m, 4H), 3.53 (t, 2H, J=6Hz), 3.95–4.53 (m, 5H), 5.15–5.53 (m, 1H), 6.05–6.45 (m, 1H), 7.80 (d, 1H, J=6Hz) | 85 |

TABLE 4

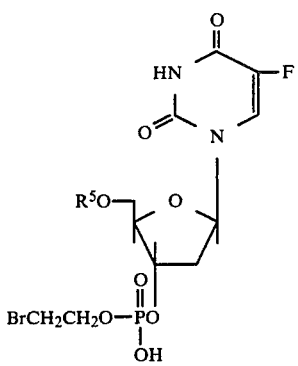

| Compound R[5] | State | IR cm[-1] | NMR (CDCl$_3$:CD$_3$OD = 2:1) δ value | Yield (%) |
|---|---|---|---|---|
| CH$_3$(CH$_2$)$_{16}$C(O)— | Waxy | (KBr) 2920, 2850, 1720, 1705, 1670, 1460, 1355, 1260, 1190, 1090, 1065, 1010, 960 | 0.89 (t, 3H, J=5Hz), 1.03–1.85 (m, 30H), 2.15–2.67 (m, 4H), 3.56 (t, 2H, J=6Hz), 4.05–4.65 (m, 5H), 4.67–5.15 (m, 1H), 6.05–6.42 (m, 1H), 7.74 (d, 1H, J=6Hz) | 54 |
| CH$_3$(CH$_2$)$_{10}$C(O)— | Oily | (Neat) 2910, 2840, 1720, 1700, 1660, 1455, 1350, 1260, 1185, 1090, 1055, 1010, 965 | 0.89 (t, 3H, J=5Hz), 1.05–1.85 (m, 18H), 2.15–2.68 (m, 4H), 3.60 (t, 2H, J=6Hz), 4.05–4.62 (m, 5H), 4.68–5.18 (m, 1H), 6.05–6.38 (m, 1H), 7.76 (d, 1H, J=6Hz) | 60 |

TABLE 4-continued

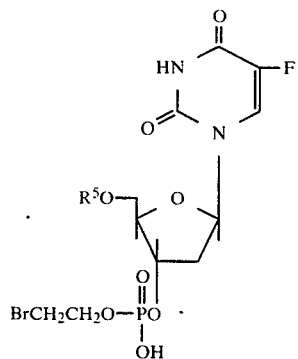

| Compound $R^5$ | State | IR cm$^{-1}$ | NMR (CDCl$_3$:CD$_3$OD = 2:1) δ value | Yield (%) |
|---|---|---|---|---|
| CH$_3$(CH$_2$)$_4$C(O)— | Oily | (Neat) 2950, 2860, 1720, 1700, 1660, 1460, 1355, 1260, 1205, 1170, 1090, 1060, 1010, 965 | 0.89 (t, 3H, J=5Hz), 1.03–1.90 (m, 6H), 2.05–2.75 (m, 4H), 3.56 (t, 2H, J=6Hz), 4.03–4.60 (m, 5H), 4.65–5.20 (m, 1H), 6.03–6.41 (m, 1H), 7.68 (d, 1H, J=6Hz) | 71 |
| CH$_3$(CH$_2$)$_7$CH=CH(CH$_2$)$_7$C(O)— | Waxy | (KBr) 2920, 2850, 1720, 1705, 1670, 1460, 1360, 1265, 1200, 1090, 1060, 1015, 960 | 0.89 (t, 3H, J=5Hz), 1.05–2.70 (m, 30H), 3.60 (t, 2H, J=6Hz), 4.03–4.63 (m, 5H), 4.65–5.15 (m, 1H), 5.18–5.49 (m, 2H), 6.08–6.47 (m, 1H), 7.75 (d, 1H, J=6Hz) | 58 |
| CH$_3$(CH$_2$)$_{14}$C(O)— | Waxy | (KBr) 2920, 2850, 1720, 1700, 1670, 1460, 1355, 1260, 1190, 1090, 1060, 1010, 960 | 0.89 (t, 3H, J=5Hz), 1.03–1.85 (m, 26H), 2.10–2.65 (m, 4H), 3.52 (t, 2H, J=6Hz), 4.04–4.63 (m, 5H), 4.65–5.20 (m, 1H), 6.05–6.40 (m, 1H), 7.62 (d, 1H, J=6Hz) | 52 |

(2)
5-Fluoro-2'-deoxy-3'-O-palmitoyl-β-uridine-5'-(2-trimethylammonioethyl)phosphate.hydrate In 20 ml of toluene was dissolved 1.01 g of 5-fluoro-2'-deoxy-3'-O-palmitoyl-β-uridine-5'-(2-bromoethyl)-phosphate, and 2 ml of anhydrous trimethylamine was added to the resulting mixture, after which the resulting mixture was subjected to reaction at 30° C. for 8 hours in a sealed tube. Subsequently, the reaction mixture was concentrated under reduced pressure, and the residue thus obtained was dissolved in 50 ml of a mixed solvent of chloroform and methanol (1:1) by volume), after which the resulting solution was washed with two 20-ml portions of water. The solvent was removed by distillation under reduced pressure, and the residue thus obtained was purified by a column chromatography (Wako Silica Gel C-200, eluant: chloroform:methanol:-water=65:25:4 by volume), to obtain 0.95 g of white, amorphous 5-fluoro-2'-deoxy-3'-O-palmitoyl-β-uridine-5'-(2-trimethylammonioethyl)phosphate.hydrate (yield 95%).

Melting point: 230°–235° C. (decomp.)

IR (KBr) cm$^{-1}$: 3430, 2920, 2850, 1720, 1670, 1460, 1250, 1090, 1060, 970

NMR (CDCl$_3$:CD$_3$OD=2:1 mixed solvent) δ values: 0.88 (t, 3H, J=5 Hz), 1.00–1.85 (m, 26H), 2.02–2.60 (m, 4H), 3.27 (s, 9H), 3.50–3.85 (m, 2H), 3.85–4.60 (m, 5H), 5.15–5.50 (m, 1H), 6.05–6.45 (m, 1H), 8.03 (d, 1H, J=6 Hz)

Reaction was effected in the same manner as above using the compounds indicated in Tables 3 and 4 to obtain the compounds shown in Tables 5 and 6.

TABLE 5

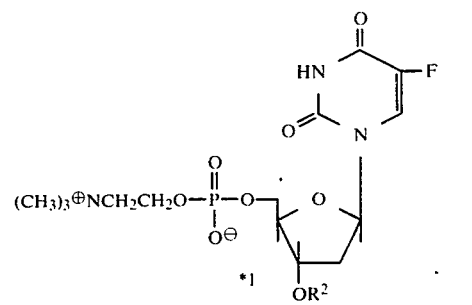

| Compound R² | m.p. (°C.) | IR (KBr) cm⁻¹ | NMR (CDCl₃:CD₃OD = 2:1) δ value | Yield (%) |
|---|---|---|---|---|
| $CH_3(CH_2)_{16}\overset{O}{\underset{\|}{C}}-$ | 235–240 (decomp.) | 3430, 2920, 2850, 1720, 1670, 1460, 1255, 1090, 1060, 970 | 0.88 (t, 3H, J=5Hz), 1.00–1.85 (m, 30H), 2.02–2.60 (m, 4H), 3.27 (s, 9H), 3.50–3.85 (m, 2H), 3.85–4.60 (m, 5H), 5.15–5.50 (m, 1H), 6.05–6.45 (m, 1H), 8.02 (d, 1H, J=6Hz) | 95 |
| $CH_3(CH_2)_7CH=CH(CH_2)_7\overset{O}{\underset{\|}{C}}-$ | 220–225 (decomp.) | 3430, 2920, 2850, 1710, 1660, 1460, 1240, 1170, 1085, 1060, 965 | 0.89 (t, 3H, J=5Hz), 1.02–1.85 (m, 22H), 1.85–2.56 (m, 8H), 3.28 (s, 9H), 3.48–3.86 (m, 2H), 3.86–4.56 (m, 5H), 5.09–5.53 (m, 3H), 6.01–6.40 (m, 1H), 8.04 (d, 1H, J=6Hz) | 70 |
| $CH_3(CH_2)_4\overset{O}{\underset{\|}{C}}-$ | 205–210 (decomp.) | 3430, 2920, 2850, 1720, 1660, 1460, 1240, 1165, 1085, 1050, 960 | 0.89 (t, 3H, J=5Hz), 1.07–1.88 (m, 6H), 2.08–2.55 (m, 4H), 3.24 (s, 9H), 3.48–3.75 (m, 2H), 3.86–4.55 (m, 5H), 5.13–5.42 (m, 1H), 6.07–6.43 (m, 1H), 7.98 (d, 1H, J=6Hz) | 85 |
| $CH_3(CH_2)_{10}\overset{O}{\underset{\|}{C}}-$ | 208–210 (decomp.) | 3430, 2920, 2850, 1710, 1670, 1460, 1240, 1165, 1085, 1060, 965 | 0.89 (t, 3H, J=5Hz), 1.05–1.85 (m, 18H), 2.10–2.60 (m, 4H), 3.30 (s, 9H), 3.55–3.85 (m, 2H), 3.95–4.55 (m, 5H), 5.20–5.54 (m, 1H), 6.08–6.48 (m, 1H), 8.06 (d, 1H, J=6Hz) | 55 |
| $CH_3(CH_2)_{12}\overset{O}{\underset{\|}{C}}-$*2 | 213–216 (decomp.) | 3430, 2920, 2850, 1710, 1670, 1460, 1245, 1160, 1085, 1055, 965 | 0.88 (t, 3H, J=5Hz), 1.00–1.75 (m, 22H), 2.07, 2.54 (m, 4H), 3.26 (s, 9H), 3.48–3.75 (m, 2H), 3.85–4.49 (m, 5H), 5.15–5.46 (m, 1H), 6.03–6.44 (m, 1H), 8.10 (d, 1H, J=6Hz) | 65 |

Note:

*1 Hydrate

*2 Reaction was effected in the same manner without isolating 5-fluoro-2'-deoxy-3'-O—acyl-β-uridine-5'-(2-bromoethyl)phosphate to obtain the objective compound.

TABLE 6

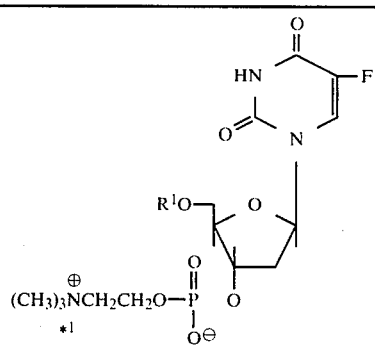

| Compound R¹ | Physical properties | | | Yield (%) |
|---|---|---|---|---|
| | m.p. (°C.) | IR (KBr) cm⁻¹ | NMR (CDCl₃:CD₃OD = 2:1) δ value | |
| $CH_3(CH_2)_{16}\overset{O}{\underset{\|}{C}}-$ | 219–223 (decomp.) | 3430, 2920, 2850, 1720, 1710, 1670, 1460, 1360, 1265, 1245, 1085, 970 | 0.89 (t, 3H, J=5Hz), 1.03–1.85 (m, 30H), 2.10–2.68 (m, 4H), 3.25 (s, 9H), 3.50–3.78 (m, 2H), 4.02–4.57 (m, 5H), 4.57–4.96 (m, 1H), 6.00–6.40 (m, 1H), 7.70 (d, 1H, J=6Hz) | 70 |
| $CH_3(CH_2)_{10}\overset{O}{\underset{\|}{C}}-$ | 197–199 (decomp.) | 3430, 2920, 2850, 1710, 1670, 1460, 1355, 1265, 1250, 1090, 970 | 0.89 (t, 3H, J=5Hz), 1.03–1.85 (m, 18H), 2.10–2.70 (m, 4H), 3.28 (m, 9H), 3.51–3.83 (m, 2H), 4.02–4.55 (m, 5H), 4.55–4.97 (m, 1H), 6.02–6.40 (m, 1H), 7.80 (d, 1H, J=6Hz) | 64 |
| $CH_3(CH_2)_7CH=CH(CH_2)_7\overset{O}{\underset{\|}{C}}-$ | 216–220 (decomp.) | 3430, 2920, 2850, 1720, 1710, 1670, 1460, 1355, 1265, 1245, 1080, 970 | 0.89 (t, 3H, J=5Hz), 1.04–2.70 (m, 30H), 3.23 (s, 9H), 3.50–3.80 (m, 2H), 4.03–4.57 (m, 5H), 4.57–4.97 (m, 1H), 5.15–5.47 (m, 2H), 6.04–6.40 (m, 1H), 7.75 (d, 1H, J=6Hz) | 64 |
| $CH_3(CH_2)_{14}\overset{O}{\underset{\|}{C}}-$ | 218–222 (decomp.) | 3430, 2920, 2850, 1720, 1710, 1670, 1460, 1360, 1265, 1245, 1085, 970 | 0.89 (t, 3H, J=5Hz), 1.03–1.85 (m, 26H), 2.10–2.70 (m, 4H), 3.28 (s, 9H), 3.52–3.81 (m, 2H), 4.03–4.56 (m, 5H), 4.56–4.95 (m, 1H), 6.02–6.38 (m, 1H), 7.72 (d, 1H, J=6Hz) | 71 |

Note:
*¹Hydrate

EXAMPLE 2

5-Fluoro-2'-deoxy-3'-O-palmitoyl-β-uridine-5'-[2-(4-dimethlaminopyridinio)ethyl]phosphate.hydrate In 5 ml of toluene was dissolved 0.27 g of 5-fluoro-2'-deoxy-3'-O-palmitoyl-β-uridine-5'-(2-bromoethyl)phosphate, and 0.2 g of 4-dimethylaminopyridine was added to the resulting solution, after which the resulting mixture was subjected to reaction at 70° C. for 4 hours. Subsequently, the solvent was removed by distillation under reduced pressure, and the residue thus obtained was dissolved in 20 ml of a mixed solvent of chloroform and methanol (1:1 by volume), and the resulting solution was washed successively with 5 ml of dilute hydrochloric acid and 5 ml of water. The solvent was removed by distillation under reduced pressure, and the residue thus obtained was purified by a column chromatography (wako Silica Gel C-200, eluant: chloroform:methanol:water=65:25:1–2 by volume) to obtain 0.12 g of white, amorphous 5-fluoro-2'-deoxy-3'-O-palmitoyl-β-uridine-5'-[2-(4-dimethylaminopyridinio)-ethyl]phosphate.hydrate (yield 41%).

Melting point: 210°–215° C. (decomp.)
IR (KBr) cm⁻¹: 3400, 2910, 2840, 1710, 1640, 1560, 1450, 1240, 1170, 1080, 1050, 820
NMR (CDCl₃) δ value: 0.88 (t, 3H, J=5 Hz), 1.04–1.87 (m, 26H), 2.06–2.55 (m, 4H), 3.24 (s, 6H), 3.60–3.89 (m, 2H), 3.96–4.51 (m, 7H), 5.16–5.44 (m, 1H), 6.08–6.41 (m, 1H), 6.81 (d, 2H, J=7 Hz), 7.86–8.26 (m, 3H)

EXAMPLE 3

5-Fluoro-2'-deoxy-5'-O-hexanoyl-β-uridine-3'-(2-trimethylammonioethyl)phosphate.hydrate The same procedure as in Example 1 (2) was repeated using 0.85 g of 5-fluoro-2'-deoxy-5'-O-hexanoyl-β-uridine-3'-(2-bromoethyl)phosphate and 20 ml of anhydrous trimethylamine, and the toluene was removed by distillation under reduced pressure. Subsequently, the residue thus obtained was extracted with 20 ml of n-butanol, and the extract was then washed with 10 ml of water, and thereafter purified by a column chromatography (Wako Silica Gel C-200, eluant: chloroform:methanol:water=65:25:4 by volume) to obtain 0.57 g of white, amorphous 5-fluoro-2'-deoxy-5'-O-hexanoyl-β-uridine-3'-(2-trimethylammonioethyl)phosphate.hydrate (yield 67%).

Melting point: 177°–180° C.

IR (KBr) cm$^{-1}$: 3420, 2950, 2860, 2790, 1710, 1660, 1470, 1395, 1355, 1240, 1180, 1085, 970

NMR (CDCl$_3$:CD$_3$OD=2:1) δ value: 0.89 (t, 3H, J=5 Hz), 1.05–1.80 (m, 6H), 2.08–2.65 (m, 4H), 3.28 (s, 9H), 3.48–3.85 (m, 2H), 4.02–4.55 (m, 5H), 4.55∝4.97 (m, 1H), 6.02–6.40 (m, 1H), 7.71 (d, 1H, J=6 Hz)

EXAMPLE 4

5-Fluoro-2'-deoxy-5'-O-palmitoyl-β-uridine-3'-[2-(2H-1,2,4-triazol-1-io)ethyl]phosphate.hydrate In 5 ml of toluene was dissolved 0.27 g of 5-fluoro-2'-deoxy-5'-O-palmitoyl-β-uridine-3'-(2-bromoethyl) phosphate, and 0.11 g of 1,2,4-triazole was added to the resulting solution, after which the resulting mixture was subjected to reaction at 70° C. for 8 hours. Subsequently, the solvent was removed by distillation under reduced pressure, and the residue thus obtained was dissolved in 20 ml of a mixed solvent of chloroform and methanol (1:1 by volume), and the resulting solution was washed successively with 5 ml of dilute hydrochloric acid and 5 ml of water. The solvent was removed by distillation under reduced pressure, and the residue thus obtained was purified by a column chromatography (Wako Silica Gel C-200, eluant: chloroform:methanol:water=65:25:1–4 by volume), to obtain 0.17 g of white, amorphous 5-fluoro-2'-deoxy-5'-O-palmitoyl-β-uridine-3'-[2-(2H-1,2,4-triazol-1-io)ethyl]phosphate.hydrate (yield 64 %).

Melting point: 185°–188° C.

IR (KBr) cm$^{-1}$: 3430, 2920, 2850, 1720, 1700, 1660, 1455, 1350, 1260, 1240, 1200, 1090, 1055, 1005, 930

NMR (CDCl$_3$:CD$_3$OD=2:1) δ value: 0.89 (t, 3H, J=5Hz), 1.03–1.80 (m, 26H), 2.05–2.62 (m, 4H), 3.84–5.08 (m, 8H), 5.95–6.38 (m, 1H), 7.71 (d, 1H, J=6 Hz), 9.07–9.42 (bs, 2H)

EXAMPLE 5

5-Fluoro-2'-deoxy-5'-O-palmitoyl-β-uridine-3'-[2-(2-hydroxyethyldimethylammonio)ethyl]phosphate.hydrate In 5 ml of toluene was dissolved 0.27 g of 5-fluoro-2'-deoxy-5'-O-palmitoyl-β-uridine-3'-(2-bromoethyl)phosphate, and 0.14 g of N,N-dimethylethanolamine was added to the resulting solution, after which the resulting mixture was subjected to reaction at 70° C. for 2 hours. Subsequently, the reaction mixture was treated and purified in the same manner as in Example 4, to obtain 0.10 g of white, amorphous 5-fluoro-2'-deoxy-5'-O-palmitoyl-β-uridine-3'-[2-(2-hydroxyethyldimethylammonio)ethyl]phosphate.hydrate (yield 36%).

Melting point: 220°–223° C. (decomp.)

IR (KBr) cm$^{-1}$: 3420, 2920, 2850, 1710, 1670, 1460, 1355, 1260, 1240, 1070, 1005, 965

NMR (CDCl$_3$:CD$_3$OD=2:1) δ value: 0.89 (t, 3H, J=5 Hz), 1.03–1.85 (m, 26H), 2.10–2.60 (m, 4H), 3.26 (s, 6H), 3.45–4.98 (m, 12H), 6.00–6.38 (m, 1H), 7.70 (d, 1H, J=6 Hz)

EXAMPLE 6

5-Fluoro-2'-deoxy-5'-O-palmitoyl-β-uridine-3'-{2-[4-(4-methyl)morpholinio]ethyl}phosphate.hydrate In 5 ml of toluene was dissolved 0.27 g of 5-fluoro-2'-deoxy-5'-O-palmitoyl-β-uridine-3'-(2-bromoethyl)phosphate, and 0.40 g of N-methylmorpholine was added to the resulting solution, after which the resulting mixture was subjected to reaction at room temperature for 3 days. Subsequently, the reaction mixture was treated and purified in the same manner as in Example 4 to obtain 0.071 g of white, amorphous 5-fluoro-2'-deoxy-5'-O-palmitoyl-β-uridine-3'-{2-[4-(4-methyl)morpholinio]ethyl}phosphate.hydrate (yield 25%).

Melting point: 217°–220° C. (decomp.)

IR (KBr) cm$^{-1}$: 3400, 2920, 2850, 1720, 1700, 1660, 1460, 1350, 1260, 1240, 1120, 1080, 1060, 1000, 960

NMR (CDCl$_3$:CD$_3$OD=2:1) δ value: 0.89 (t, 3H, J=5 Hz), 1.03–1.85 (m, 26H), 2.10–2.66 (m, 4H), 3.34 (s, 3H), 3.40–4.50 (m, 15H), 4.55–4.98 (m, 1H), 6.02–6.41 (m, 1H), 7.73 (d, 1H, J=6 Hz)

EXAMPLE 7

5-Fluoro-2'-deoxy-5'-O-palmitoyl-β-uridine-3'-[2-(1-pyrazolyl)ethyl]phosphate.hydrate In 5 ml of toluene was dissolved 0.27 g of 5-fluoro-2'-deoxy-5'-O-palmitoyl-β-uridine-3'-(2-bromoethyl)phosphate, and 0.27 g of pyrazole was added to the resulting solution, after which the resulting mixture was subjected to reaction at 70° C. for 8 hours. Subsequently, the solvent was removed by distillation under reduced pressure, and the residue thus obtained was dissolved in 20 ml of a mixed solvent of chloroform and methanol (1:1 by volume), after which the resulting solution was washed successively with 5 ml of dilute hydrochloric acid and 5 ml of water. The solvent was removed by distillation under reduced pressure, and the residue thus obtained was purified by a column chromatography (Wako Silica Gel C-200, eluant: chloroform:methanol=20:1–10:1 by volume), to obtain 0.18 g of white, amorphous 5-fluoro-2'-deoxy-5'-O-palmitoyl-β-uridine-3'-[2-(1-pyrazolyl)ethyl]phosphate.hydrate (yield 68%).

Melting point: 78°–82° C.

IR (KBr) cm$^{-1}$: 3410, 2920, 2850, 1710, 1670, 1460, 1355, 1265, 1250, 1190, 1120, 1090, 1050, 1010, 950

NMR (CDCl$_3$:CD$_3$OD=2:1) δ value: 0.89 (t, 3H, J=5 Hz), 1.03–1.85 (m, 26H), 2.05–2.60 (m, 4H), 3.90–4.95 (m, 8H), 5.92–6.42 (m, 2H), 7.43–7.88 (m, 3H).

PREPARATION EXAMPLE 1

500 ml of an aqueous solution (0.2 w/v %) of 5-fluoro-2'-deoxy-3'-O-oleoyl-β-uridine-5'-(2-trimethylammonioethyl)phosphate.hydrate was sterilely filtered, and the filtrate thus obtained was divided and poured into vials having a 20 ml capacity in a proportion of 12.5 ml/vial, and then freeze-dried in a conventional manner to obtain 4,000 vials of white, freeze-dried product (25 mg/vial).

PREPARATION EXAMPLE 2

500 ml of an aqueous solution (0.4 w/v %) of 5-fluoro-2'-deoxy-5'-hexanoyl-β-uridine-3'-(2-trimethylammonioethyl)phosphate.hydrate was sterilely filtered, and the filtrate thus obtained was divided and poured into vials having a 20 ml capacity in a proportion of 12.5 ml/vial, and then freeze-dried in a conventional manner to obtain 2,000 vials of white, freeze-dried product (50 mg/vial).

What is claimed is:

1. A 5-fluoro-2'-deoxyuridine derivative represented by the general formula [I] or a salt thereof:

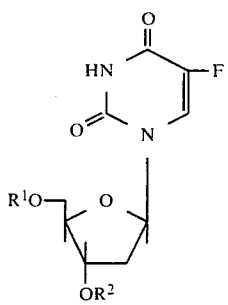

wherein $R^1$ and $R^2$ are different from each other, one of which represents a $C_{1-30}$aliphatic carboxylic acid residue and the other represents a group represented by the formula,

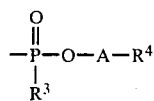

in which $R^3$ represents an oxido group, A represents a $C_{1-5}$-alkylene group and $R^4$ represents a tri-$C_{1-4}$alkylammonio, pyridinio, pyridazinio, pyrimidinio, pyrazinio, 2H-imidazolio, 3H-imidazolio, 2H-pyrazolio, 1-methylpiperidinio, 4-methylmorpholinio or 2H-1,2,4-triazol-1-io, which may be substituted by at least one substituent selected from the group consisting of hydroxyl, $C_{1-4}$alkoxy, acetyloxy, propionyloxy, $C_{1-4}$alkyl and di-$C_{1-4}$alkyl-amino groups.

2. A 5-fluoro-2'-deoxyuridine derivative or a salt thereof according to claim 1, wherein $R^1$ is a group represented by the formula,

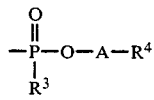

wherein $R^3$ and A have the same meanings as defined in claim 1, $R^4$ is a tri-$C_{1-4}$alkylammonio, pyridinio, pyridazinio, pyrimidinio, pyrazinio, 2H-imidazolio, 3H-imidazolio, 2H-pyrazolio, 1-methylpiperidinio, 4-methylmorpholinio or 2H-1,2,4-triazol-1-io group; and $R^2$ is a $C_{1-30}$-aliphatic carboxylic acid residue.

3. A 5-fluoro-2'-deoxyuridine derivative or a salt thereof according to claim 2, wherein A is an ethylene group.

4. A 5-fluoro-2'-deoxyuridine derivative or a salt thereof according to claim 3, wherein $R^4$ is a tri-$C_{1-4}$-alkylammonio group.

5. A 5-fluoro-2'-deoxyuridine derivative or a salt thereof according to claim 4, wherein $R^4$ is a trimethylammonio group.

6. A 5-fluoro-2'-deoxyuridine derivative or a salt thereof according to one of claims 2, 3, 4 and 5, wherein $R^2$ is a $C_{6-18}$aliphatic carboxylic acid residue.

7. A 5-fluoro-2'-deoxyuridine derivative or a salt thereof according to claim 1, wherein $R^1$ is a $C_{1-30}$aliphatic carboxylic acid residue and $R^2$ is a group represented by the formula,

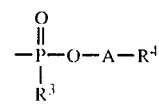

wherein $R^3$, $R^4$ and A have the same meanings as defined in claim 1.

8. A 5-fluoro-2'-deoxyuridine derivative or a salt thereof according to claim 7, wherein A is an ethylene group.

9. A 5-fluoro-2'-deoxyuridine derivative or a salt thereof according to claim 8, wherein $R^4$ is a tri-$C_{1-4}$-alkylammonio group.

10. A 5-fluoro-2'-deoxyuridine derivative or a salt thereof according to claim 9, wherein $R^4$ is a trimethylammonio group.

11. A 5-fluoro-2'-deoxyuridine derivative or a salt thereof according to one of claims 7, 8, 9 and 10, wherein $R^1$ is a $C_{6-18}$aliphatic carboxylic acid residue.

12. A 5-fluoro-2'-deoxyuridine derivative or a salt thereof according to claim 1, wherein the derivative is 5-fluoro-2'-deoxy-3'-O-stearoyl-$\beta$-uridine-5'-(2-trimethylammonioethyl)phosphate.

13. A 5-fluoro-2'-deoxyuridine derivative or a salt thereof according to claim 1, wherein the derivative is 5-fluoro-2'-deoxy-3'-O-oleoyl-$\beta$-uridine-5'-(2-trimethylammonioethyl)phosphate.

14. A 5-fluoro-2'-deoxyuridine derivative or a salt thereof according to claim 1, wherein the derivative is 5-fluoro-2'-deoxy-5'-O-oleoyl-$\beta$-uridine-3'-(2-trimethylammonioethyl)phosphate.

15. A 5-fluoro-2'-deoxyuridine derivative or salt thereof according to claim 1, wherein the derivative is 5-fluoro-2'-deoxy-5'-O-hexanoyl-$\beta$-uridine-3'-(2-trimethylammonioethyl)phosphate.

16. A pharmaceutical composition useful for treating tumors in a host mammal which comprises an effective amount of the compound in claim 1, in combination with a pharmaceutically acceptable inert excipient, diluent or carrier.

* * * * *